(12) United States Patent
Mueller et al.

(10) Patent No.: US 7,303,903 B2
(45) Date of Patent: Dec. 4, 2007

(54) PRODUCTION OF WEAKLY ACTIVE OR INACTIVE MUTANTS OF ALKALINE PHOSPHATASE AND THEIR EXPRESSION IN YEAST

(75) Inventors: Rainer Mueller, Penzberg (DE); Johann-Peter Thalhofer, Weilheim (DE); Frank Geipel, Penzberg (DE); Werner Hoelke, Penzberg (DE); Thomas Kirschbaum, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/712,877

(22) Filed: Mar. 1, 2007

(65) Prior Publication Data

US 2007/0154941 A1    Jul. 5, 2007

Related U.S. Application Data

(62) Division of application No. 10/395,790, filed on Mar. 24, 2003, now Pat. No. 7,202,072.

(30) Foreign Application Priority Data

Mar. 25, 2002    (DE)    ................ 102 13 201

(51) Int. Cl.
| | |
|---|---|
| C12P 21/06 | (2006.01) |
| C12N 15/00 | (2006.01) |
| C12N 5/10 | (2006.01) |
| C12N 1/21 | (2006.01) |
| C12N 1/15 | (2006.01) |
| C12N 1/19 | (2006.01) |
| C07H 21/04 | (2006.01) |
| C12N 9/16 | (2006.01) |
| C07K 14/00 | (2006.01) |

(52) U.S. Cl. .................. 435/196; 435/320.1; 435/69.1; 435/252.3; 435/254.2; 435/254.23; 435/325; 530/350; 536/23.1; 536/23.2

(58) Field of Classification Search ................ 435/196, 435/320.1, 59.1, 325, 254.2, 254.23, 252.3, 435/69.1; 536/23.1, 23.2; 530/350
See application file for complete search history.

*Primary Examiner*—Delia M. Ramirez
(74) *Attorney, Agent, or Firm*—Marilyn L. Amick; Roche Diagnostics Operations, Inc.

(57) ABSTRACT

The invention concerns a method for the recombinant production or expression of eukaryotic alkaline phosphatase mutants in yeast cells wherein the specifically introduced mutations result in a reduction of the specific AP activity by at least a factor 1:100. The invention also concerns a method for inserting corresponding nucleic acid sequences into a vector for expression in methylotrophic yeast strains and it concerns corresponding vectors and host strains.

14 Claims, 2 Drawing Sheets

PRODUCTION OF WEAKLY ACTIVE OR INACTIVE MUTANTS OF ALKALINE PHOSPHATASE AND THEIR EXPRESSION IN YEAST

RELATED APPLICATIONS

This application is a divisional of U.S. application Ser. No. 10/395,790 filed Mar. 24, 2003, now U.S. Pat. No. 7,202,072 issued Apr. 10, 2007, and claims priority tn German application DE 10213201.1 filed Mar. 25, 2002.

FIELD OF THE INVENTION

The invention concerns a method for the recombinant production and expression of mutants of a eukaryotic alkaline phosphatase which is weakly active or inactive. In addition the invention concerns codon-optimized DNAs based on the nucleic acid sequence which codes for a highly-active alkaline phosphatase and which has been modified by directed mutagenesis in such a manner that it codes for an alkaline phosphatase which has only a weak activity or is inactive. The invention also concerns a method for inserting the mutated DNA into a vector for expression in yeast cells and a method for expressing the alkaline phosphatase mutants in yeast.

BACKGROUND

Alkaline phosphatases (AP) are dimeric, zinc-containing, non-specific phosphomono-esterases which occur in prokaryotic and eukaryotic organisms e.g. in *E. coli* and mammals (McComb et al., 1979 *Alkaline Phosphatases* Plenum Press, New York). A comparison of the primary structure of various alkaline phosphatases showed that there is a high degree of homology (25-30% homology between *E. coli* and mammalian AP; Millàn, 1988 *Anticancer Res.* 8, 995-1004; Harris, 1989 *Clin. Chim. Acta* 186, 133-150).

In humans and higher animals the AP family consists of four members which are coded in different gene loci (Millàn, 1988 *Anticancer Res.* 8, 995-1004; Harris 1989 *Clin. Chim. Acta* 186, 133-150). The family of alkaline phosphatases includes the tissue-specific APs (placental AP (PLAP), germ cell AP (GCAP) and intestinal AP (IAP)) and the non-tissue-specific APs (TnAP) which are mainly located in the liver, kidney and bones.

An important property of the previously known APs is the large variability in the catalytic activity of mammalian APs which have a 10-100-fold higher $k_{cat}$s value than *E. coli* AP. Among the mammalian APs the APs from the bovine intestine (bIAP) exhibit the highest specific activities. This property makes the bIAPs attractive for biochemical applications such as e.g. the use of corresponding enzyme conjugates as a diagnostic reagent or for dephosphorylating DNA. The existence of various alkaline phosphatases from the bovine intestine which have different levels of specific activity is described in EP 0955 369 and Manes et al. (1998), *J. Biol. Chem.* 273 No. 36, 23353-23360. Up to now recombinant expression of eukaryotic alkaline phosphatases of low activity (up to 3000 U/mg) has been described in various eukaryotic cell lines such as CHO cells (bIAP I/WO 93/18139; Weissig et al. 1993, *Biochem. J.* 260, 503-508), COS cells (human placental AP/Berger et al. 1987 *Biochemistry* 84, 4885-4889) or baculovirus expression system (human placental AP/Davis et al. 1992, *Biotechnology* 10, 1148-1150). The expression of APs having a higher activity (spec. activity>3000 U/mg) from the bovine intestine in CHO cells has also been described (bIAP II, III and IV/Manes et al. 1998, *J. Biol. Chem.* 273 No. 36, 23353-23360). However, a disadvantage of expressing alkaline phosphatases in these expression systems is the low expression rate which makes it uneconomical to produce eukaryotic alkaline phosphatase recombinantly.

Although in principle it is possible to express eukaryotic alkaline phosphatases in prokaryotic expression hosts such as *E. coli* (human placental AP/Beck and Burtscher, 1994 *Protein Expression and Purification* 5, 192-197), the alkaline phosphatases expressed in prokaryotes have no glycosylation which is essential especially for the preparation of enzyme conjugates depending on the conjugate method.

Alkaline phosphatase is often used as an enzyme conjugate in the form of a complex with an antibody. In this case the alkaline phosphatase is conjugated with an antibody which is directed against a particular antigen. This antigen is firstly bound in a first reaction by an antibody immobilized on a vessel wall which recognizes a different epitope on the target antigen than does the antibody-AP conjugate. This antibody-antigen complex is then detected in a second reaction by the binding of the antibody-AP conjugate. False-positive results occur repeatedly in such tests and are caused by an unspecific binding of the antibody-AP conjugate to the vessel wall or to the first antibody. These interferences can be prevented by adding an excess of a conjugate containing an inactive or weakly active AP mutant as an interference-eliminating protein. However, in order to act very specifically as an interference-eliminating protein, the AP mutant must, in addition to having a low activity or no activity, also have essentially the same tertiary and quaternary structure.

Hence the object of the present invention is to use directed mutagenesis to produce mutants of alkaline phosphatase as an interference-eliminating protein which are only very weakly-active or completely inactive but whose amino acid sequence is only slightly modified and have a tertiary and quaternary structure that is changed as little as possible. Another object of the invention is to develop a robust and stable expression method for producing glycosylated eukaryotic alkaline phosphatase mutants which also enables an economical production of a corresponding alkaline phosphatase mutant due to the high expression rate.

SUMMARY OF THE INVENTION

The present invention concerns mutants of eukaryotic alkaline phosphatase wherein the sequence to be mutated is at least 77% homologous to SEQ ID NO: 2, the mutant has an activity which is reduced by at least 100-fold compared to the wild-type, and the mutant has one or more of the following mutations, with the position of the mutation defined relative to the position in SEQ ID NO: 2:

Asp42 for Asn, Val, Ala or Ser

Ser92 for Ala, Gly, Val or Leu

Ser155 for Ala, Gly, Val or Leu

Glu311 for Gln, Asn, Leu, Ile or Met

Asp316 for Asn, Val, Ala or Ser

His320 for Asn, Phe, Asp or Tyr,

Gly322 for any amino acid larger than Asp such as Phe, Trp, Arg, Lys, Glu, Gln, His, Tyr or Ile Asp357 for Asn, Val, Ala or Ser His358 for Asn, Phe, Asp or Tyr His432 for Asn, Phe, Asp or Tyr

DETAILED DESCRIPTION OF THE INVENTION

Figure 1:
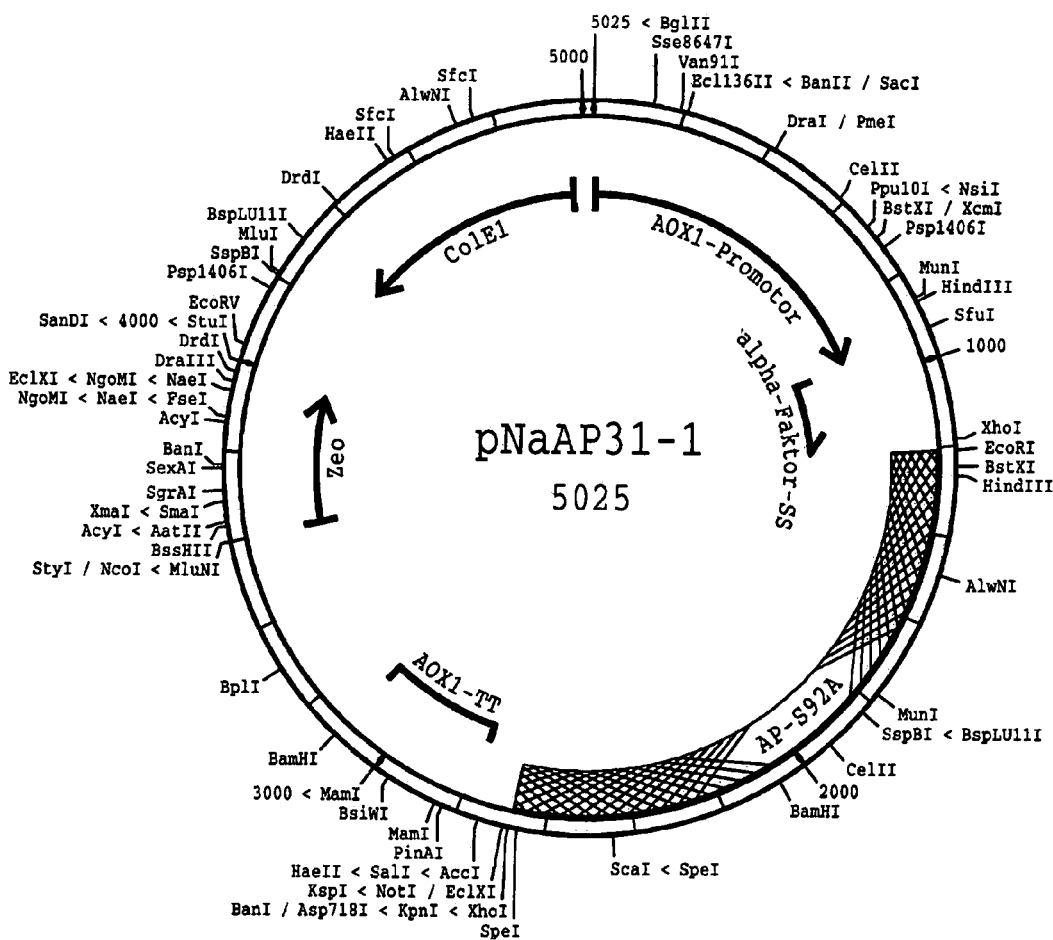
FIG. 1: Plasmid map of the expression vector pNaAP31-1 combing the mutated gene sequence according to SEQ ID NO: 8 in pICZαA (Invitrogen).

A mutation of the amino acid sequence is understood as an exchange of the naturally occurring amino acid at the desired position for any other amino acid which does not hinder folding into the correct tertiary and quaternary structure, but however, are not functional.

The sequence to be mutated (wild type) can for example be a human intestinal AP or a human placental AP. In addition an AP of low activity or high activity from bovine intestine also come into consideration as the wild-type AP according to the invention. All these enzymes are at least 77% homologous to SEQ ID NO: 2. The homology was determined with the software "Open VMS Vax Version V6.2"; (copyright) (c) 1982-2001, Genetics Computer Group, Inc.; A wholly owned subsidiary of Oxford Molecular Group, Inc. All rights reserved. Published research assisted by this software should cite: Wisconsin Package Version 10.2, Genetics Computer Group (GCG), Madison, Wis.).

The stated position of the amino acid to be mutated relates to the amino acid sequence of native alkaline phosphatase according to SEQ ID NO: 2, without a signal sequence. However, the stated amino acid positions are also transferable to other bovine alkaline phosphatases or alkaline phosphatases from other organisms; the exchanges affect amino acids with highly conserved functions within the protein and hence it is only necessary to adapt the position after the respective amino acid sequence.

Directed mutagenesis of the DNA sequence means that one or more codons are changed by means of PCR mutagenesis. In this process only as few changes as necessary are changed in the base triplet of the codon-optimized gene according to SEQ ID NO: 3 and in the most favourable case only one base is changed.

Mutants of the eukaryotic alkaline phosphatase are preferred according to the invention in which the mutant has one or more of the following mutations and the position of the mutation is defined relative to the position in SEQ ID NO: 2.

Asp42 for Val or Asn
Ser92 for Ala or Gly
Ser155 for Ala or Gly
Glu311 for Gln or Leu
Asp316 for Val or Asn
His320 for Asn or Phe
Gly322 for Phe or Lys
Asp357 for Val or Asn
His358 for Asn or Phe
His432 for Asn or Phe The above-mentioned mutants of the eukaryotic alkaline phosphatase are preferred according to the invention in which the enzyme having the wild-type sequence has a specific activity of more than 7000 U/mg. In addition a DNA sequence is preferred as a gene sequence which is based on the gene which codes for a eukaryotic alkaline phosphatase mutant having a specific activity of more than 7000 U/mg and has been specifically mutated at a few positions such that the resulting DNA sequence codes for an amino acid sequence of the eukaryotic alkaline phosphatase mutant which is modified at one or a few positions, wherein the mutation results in a substantial to total reduction of the specific activity.

The mutants according to the invention of eukaryotic alkaline phosphatase are particularly preferred in which the mutant has an at least 1000-fold reduced AP activity compared to the wild-type enzyme. Furthermore mutants of the eukaryotic alkaline phosphatase according to the invention are preferred in which the mutant has an at least 1000-fold reduced activity compared to the corresponding wild-type enzyme. Those mutants are especially preferred according to the invention in which the reduction of the specific activity is below the detection limit (determined according to the activity test described in example 4).

The following amino acid positions have proven to be suitable according to the invention: Asp316/His320/His432 (binding partners of zinc atom 1), Asp42/Asp357/His358 (binding partners of zinc atom 2), Ser155/Glu311 (binding partners of the magnesium atom), Ser92 (hydroxyl group is deprotonated for the nucleophilic attack on the substrate) (Ma and Kantrowitz (1994), *J. Biol. Chem.* 16 pp. 31614-31619; Ma et al. (1995), Protein Science, 4, pp, 1498-1506; Kimura and Kikuta (2000) JBIC, 5, pp. 139-155; Stec et al. (2000), JMB 299 pp. 1303-1311) and Gly322 (important for the specific activity; EP 0 955 369). According to the invention the positions described above come into consideration as single mutants or also in all possible combinations of the above-mentioned positions as double, triple or multiple mutants. The mutated amino acid sequences according to SEQ ID NO's: 4-7, are particularly preferred in which SEQ ID NO: 4 represents a single mutant at position 92 (Ser92Ala), SEQ ID NO: 5 represents a single mutant at position 322 (Gly322Phe), SEQ ID NO: 6 represents a double mutant at positions 320 and 322 (His320Asn/Gly322Phe) and SEQ ID NO: 7 represents a triple mutant at positions 92, 320 and 322 (Ser92Ala/His320Asn/Gly322Phe). The respective DNA sequences are shown in SEQ ID NO: 8-11.

Figure 2:
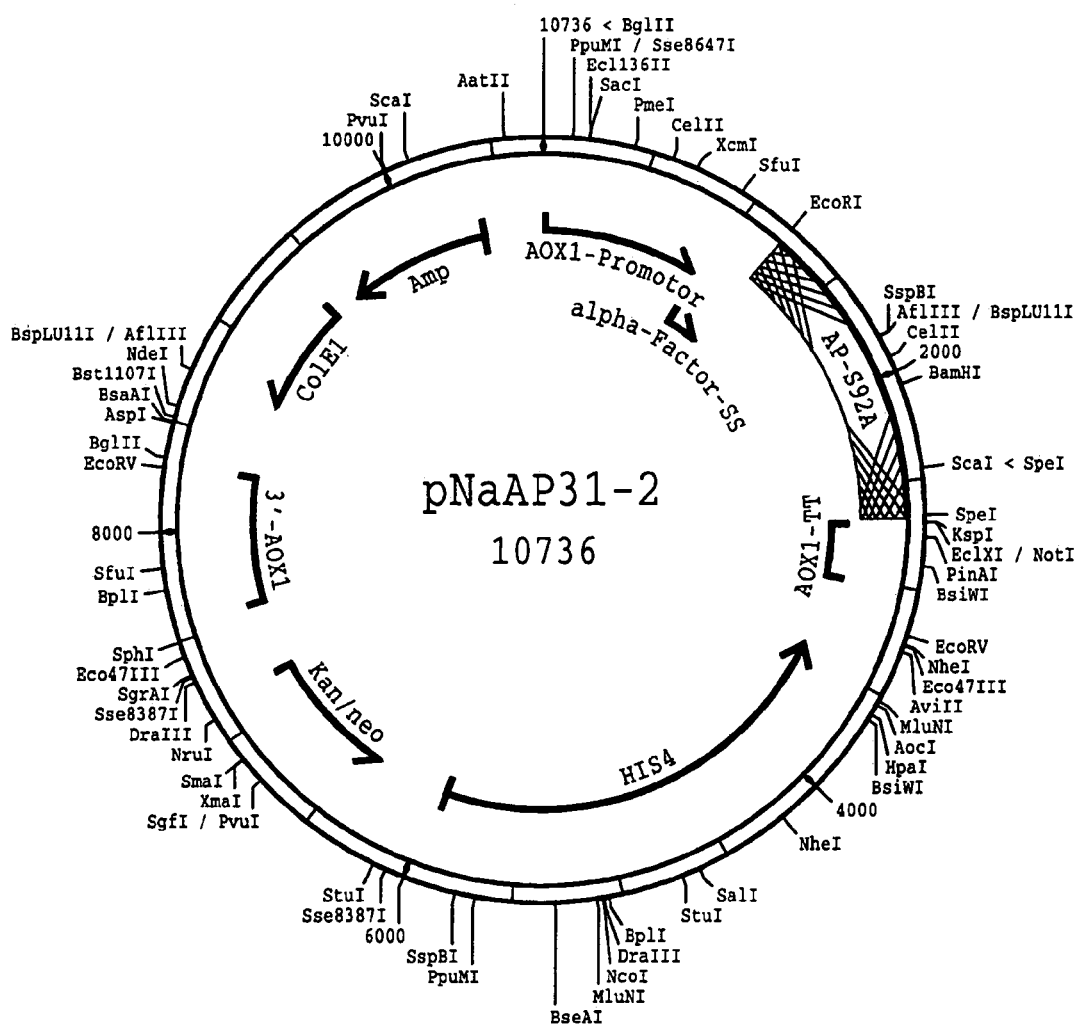
FIG. 2: Plasmid map of the expression vector pNaAP31-1 combining the mutated gene sequence according to SEQ ID NO: 8 in pIC9K (Invitrogen).

The present invention also concerns a DNA which codes for the mutant according to the invention described above. Furthermore the present invention concerns vectors which contain the nucleic acid sequence according to the invention. In particular these are vectors containing a nucleic acid sequence, wherein the nucleic acid sequence is selected from the SEQ ID NO's: 4-7. Suitable vectors are known to a person skilled in the art such as pPICZαA, B, C; pPICZ, pPICZ-E, pPICZα-E; pPIC6, pPIC6αA, B, C; pGAPZ, pGAPZαA, B, C; pPIC9; pPIC9K, pPIC3.5, pPIC3.5K, pAO815, pMET, pMETαA, B, C; pYES-DEST52, pYES2.1/V5-His-TOPO, pYC2-E, pYES2.1-E; YES vectors, pTEF1/Zeo, pTEF1/Bsd, pNMT-TOPO (e.g. Invitrogen). The corresponding gene sequences are for example cloned into the vectors pPICZαA or pPIC9K which are commercially available (Invitrogen) and which contain the gene sequences of SEQ ID NO's: 8-11 according to the invention which are under the control of the AOX1 promoter. The following are examples of vectors prepared according to the invention: vectors pNaAP31-1 (FIG. 1) and pNaAP31-2 (FIG. 2), which have the gene sequence according to SEQ ID NO: 8 each cloned into pPICZαA (pNaAP31-1) and pPIC9K (pNaAP31-2).

The vectors pNaAP31-1 and pNaAP31-1 are equally relevant for the vectors prepared according to the invention since the final production clone can contain copies of both vectors.

An expression vector obtained according to the invention is preferably transformed into various strains of yeast such as *Pichia pastoris* and stably integrated into the genome. An advantage of the stable integration into the yeast genome is in particular that no selection pressure is necessary when for example the weakly-active or inactive alkaline phosphatase mutants are subsequently produced in large volume fermentors. Stable integration into the genome means that the expression vector is incorporated into the genome of for example *Pichia pastoris* by means of homologous recombination and is thus transmitted from generation to generation as a permanent component of the yeast genome (Cregg, J. M. et al., *Mol. Cell. Biol.* 5 (1985), 3376-3385).

Another subject matter of the invention is a yeast strain transformed with one of the vectors according to the invention. Methylotrophic yeasts such as the yeast *Pichia pastoris, Hansenula polymorpha, Saccharomyces cerevisiae, Yarrowia lipolytica* or *Schizosaccharomyces pombe* are particularly suitable as the yeast host. *Pichia pastoris* is particularly preferably used as the host strain. The *Pichia pastoris* X-33 strain is particularly preferably transformed with one of the described vectors.

The invention also concerns a method for producing the mutant of the eukaryotic alkaline phosphatase according to the invention in yeast cells comprising the steps: a) cloning a gene sequence according to the invention into different vectors, b) transforming the yeast, c) expression and d) purifying the alkaline phosphatase wherein a first vector has a resistance gene to a first selection marker, transformants which have integrated the resistance gene and the desired gene sequence into the genome are selected by growth on nutrient medium containing a low concentration of a first selection marker, the gene copy number is increased by multiple transformation whereby multiple transformants are selected by growth on nutrient medium with increased selection pressure, a second vector which has a resistance gene to a second selection marker is added, the gene copy number is increased by multiple transformation whereby multiple transformants are selected by growth on nutrient medium with increased selection pressure, and those clones are selected which have stably integrated several copies of the gene sequence and of the selection marker resistance genes into the genome.

Methylotrophic yeast cells are preferably used in the method according to the invention. *Pichia pastoris* is particularly preferably used as the yeast cell.

Furthermore it is preferred that a vector is used for the method according to the invention which essentially corresponds to a vector which is selected from the following vectors: pPICZαA, B, C; pIZCZ, pPICZ-E, pPICZα-E, pPIC6, pPIC6αA, B, C; pGAPZ, pGAPZαA, B, C; pPIC9; pPIC9K, pPIC3.5, pPIC3.5 K, pAO815, (Invitrogen).

The copy number of the mutated gene sequence in the methylotrophic yeast was increased by multiple transformation while simultaneously increasing the selection pressure with a suitable selection marker e.g. an antibiotic such as Zeocin or GENETICIN (G418), after which only those clones are viable which have stably integrated several copies of the expression vector into the genome. In order to be resistant to high concentrations of the antibiotic used as the selection marker, it is necessary that the clones produce increased amounts of resistance proteins. This can for example be achieved by a multiple integration of the expression vector which, in addition to the expression cassette for the respective AP mutant e.g. the alkaline phosphatase mutant Ser92Ala, also contains the resistance gene for the antibiotic used as the selection marker.

The object of producing alkaline phosphatase mutants in a robust and stable expression method having a high expression rate and at the same time in economical yields was achieved by the method described in the following.

The directed mutagenesis for producing the mutants according to the invention was carried out as follows: based on the gene which codes for a bovine alkaline phosphatase mutant and which was prepared synthetically, oligonucleotides which were complementary to one another or which overlapped were designed in which one or several base positions were changed compared to SEQ ID NO: 3. One of these primers was subsequently used in a PCR reaction as a partner of the 5' or 3' primer described in the following and thus the AP gene was amplified in two sections containing the desired base exchange(s).

The two sections were subsequently analysed by means of agarose gel electrophoresis, the products having the expected length were isolated from the gel by means of the QIAquick gel extraction kit (QIAGEN) and synthesized in a further PCR reaction to form the complete gene product. The first five cycles of the PCR reaction were carried out without adding the primer at the 5' end and at the 3' end of the whole gene so that at first only a few fragments of the gene product of the expected length are formed from the two sections. The annealing temperature depends on the melting temperature of the overlapping region. Subsequently the terminal primers were added and the annealing temperature was increased in accordance with the annealing temperature of the primer with the lowest melting temperature. Afterwards the gene fragment of the expected length was amplified in a further 25 cycles.

The PCR mixture was analysed by means of agarose gel electrophoresis and the gene fragment having the expected size was isolated (QIAquick gel extraction kit/Qiagen).

The cloning of a corresponding PCR fragment, the transformation in *Pichia pastoris* and the expression of the corresponding AP mutant are described in example 2.

The recombinant alkaline phosphatase mutants can be isolated from the biomass by extraction methods which are in principle known to a person skilled in the art e.g. by "protein purification", Springer Publishers, Editor Robert Scopes (1982). A pure band product is achieved by suitable chromatographic methods such as in particular by using hydrophobic column materials and a cation exchanger.

Hence the present invention describes for the first time a method which allows an economical production of recombinant alkaline phosphatase mutants from mammals e.g. bovine intestine, in yeast which have a very greatly reduced AP activity or no longer have an AP activity but otherwise have properties which correspond to those of recombinant alkaline phosphatase mutants from the bovine intestine. These mutants can be used especially as interference-eliminating proteins in immunological test procedures in which AP is used as a label such as MTP-ELISA.

Legends for the Sequence Protocols SEQ ID NO's 1-21

SEQ ID NO: 1: native DNA sequence coding for highly active bovine AP without a signal sequence SEQ ID NO: 2: amino acid sequence of the highly active bovine AP SEQ ID NO: 3: DNA sequence of the synthetic gene coding for a highly active AP, the restriction cleavage site EcoRI is located upstream of the coding sequence and the restriction cleavage site Asp718 is located downstream thereof SEQ ID NO: 4: amino acid sequence of the AP single mutant Ser92Ala (wild-type: highly active bovine AP)

SEQ ID NO: 5: amino acid sequence of the AP single mutant Gly322Phe (wild-type: highly active bovine AP)

SEQ ID NO: 6: amino acid sequence of the AP double mutant His320Asn/Gly322Phe (wild-type: highly active bovine AP)

SEQ ID NO: 7: amino acid sequence of the AP triple mutant Ser92Ala/His320Asn/Gly322Phe (wild-type: highly active bovine AP)

SEQ ID NO: 8: DNA sequence of the synthetic gene coding for the AP single mutant Ser92Ala with the cleavage sites EcoRI and Asp718 located upstream and downstream respectively of the coding sequence SEQ ID NO: 9: DNA sequence of the synthetic gene coding for the AP single mutant Gly322Phe with the cleavage sites EcoRI and Asp718 located upstream and downstream respectively of the coding sequence SEQ ID NO: 10: DNA sequence of the synthetic gene coding for the AP double mutant His320Asn/Gly322Phe with the cleavage sites EcoRI and Asp718 located upstream and downstream respectively of the coding sequence SEQ ID NO: 11: DNA sequence of the synthetic gene coding for the AP triple mutant Ser92Ala/His320Asn/Gly322Phe with the cleavage sites EcoRI and Asp718 located upstream and downstream respectively of the coding sequence SEQ ID NO's: 12-21: DNA sequences which were used as primers Abbreviations
YPD: yeast peptone dextrose
YPDS: yeast peptone dextrose sorbitol
BMGY: buffered glycerol-complex medium
BMMY: buffered methanol-complex medium
MTP: microtitre plates Specific Embodiments

EXAMPLE 1

Mutagenesis of the Synthetic DNA Sequence which Codes for the Bovine Alkaline Phosphatase Mutants For the mutagenesis of the desired base triplet(s) by means of the PCR reaction, oligonucleotides were designed which have a correspondingly modified base sequence and are complementary to one another or are partially overlapping and complementary. These oligonucleotides were subsequently used as corresponding partners for the 5' primer 5'-hAP according to SEQ ID NO: 12 or for the 3' primer 3'-hAP according to SEQ ID NO: 13 which each hybridize with the 5' end or with the 3' end respectively of the gene which codes for the bovine alkaline phosphatase mutants. In this manner the mutated gene sequence was amplified in two segments in a first reaction, the first segment carrying a mutation at the 3' end and the second segment carrying a mutation at the 5' end and a short base sequence at the 3' end of the first segment being identical to a short base sequence at the 5' end of the second segment.

These two segments were then fused in a second PCR reaction to form the full length product. For this the PCR reaction was firstly started without the 5'-hAP and 3'-hAP primers according to SEQ ID NO: 12 and 13 and 5 cycles were carried out. A few molecules of the full length product are formed in this process; the annealing temperature in these 5 cycles depends on the melting temperature of the overlapping region of the two segments. Subsequently the 5' and 3' primer according to SEQ ID NO: 12 and 13 are added, the annealing temperature is adapted to the melting temperature of the primer with the lower melting temperature and the full length product is amplified in a further 25 cycles.

Mutagenesis to Generate the Single Mutant Ser92Ala

In order to generate the single mutant Ser92Ala the base triplet at position 274-276, with reference to the base triplet TTG according to SEQ ID NO: 3, which codes for the first amino acid of the highly-active bovine alkaline phosphatase was mutated from TCT into GCT. The primers 5'-S92A according to SEQ ID NO: 14 and 3'-S92A according to SEQ ID NO: 15 which are partially complementary to one another were designed for this purpose. The first PCR reaction was subsequently started with the primer pairs 5'-hAP and 3'-S92A as well as 5'-S92A and 3'-hAP separate from one another using the gene sequence according to SEQ ID NO: 3 as the template such that the mutated gene sequence was firstly amplified in two segments. The segments were analysed by an agarose gel and isolated from the agarose gel (QIAquick gel extraction kit/Qiagen) and subsequently used in the second PCR reaction. In this second PCR reaction the two segments were fused as described above to form the full length product. The mutated gene sequence formed in this manner was cloned using PCR cloning vectors (PCR cloning kit—blunt end/Roche Diagnostics) and examined by means of restriction analysis and sequencing.

Mutagenesis to Generate the Single Mutant Gly322Phe

In order to generate the single mutant Gly322Phe the base triplet at position 964-966, with reference to the base triplet TTG according to SEQ ID NO: 3, which codes for the first amino acid of the highly-active bovine alkaline phosphatase was mutated from GGT into TTT. The primers 5'-G322F according to SEQ ID NO: 16 and 3'-G322F according to SEQ ID NO: 17 which are partially complementary to one another were designed for this purpose. The first PCR reaction was subsequently started with the primer pairs 5'-hAP and 3'-G322F as well as 5'-G322F and 3'-hAP separate from one another using the gene sequence according to SEQ ID NO: 3 as the template such that the mutated gene sequence was firstly amplified in two segments. The segments were analysed by an agarose gel and isolated from the agarose gel (QIAquick gel extraction kit/Qiagen) and subsequently used in the second PCR reaction. In this second PCR reaction the two segments were fused as described above to form the full length product. The mutated gene sequence formed in this manner was cloned using PCR cloning vectors (PCR cloning kit—blunt end/Roche Diagnostics) and examined by means of restriction analysis and sequencing.

Mutagenesis to Generate the Double Mutant His320Asn/Gly322Phe

In order to generate the double mutant His320Asn/Gly322Phe, the base triplets at positions 958-960 and 964-966, with reference to the first base triplet TTG according to SEQ ID NO: 3, which codes for the first amino acid of the highly-active bovine alkaline phosphatase was mutated from CAT into AAT and GGT into TTT. The primers 5'-H320N/ G322F according to SEQ ID NO: 18 and 3'-H320N/G322F according to SEQ ID NO: 19 which are partially complementary to one another were designed for this purpose. The first PCR reaction was subsequently started with the primer pairs 5'-hAP and 3'-H320N/G322F as well as 5'-H320N/ G322F and 3'-hAP separate from one another using the gene sequence according to SEQ ID NO: 3 as the template such that the mutated gene sequence was firstly amplified in two segments. The segments were analysed by an agarose gel and isolated from the agarose gel (QIAquick gel extraction kit/Qiagen) and subsequently used in the second PCR reaction. In this second PCR reaction the two segments were fused as described above to form the full length product. The mutated gene sequence formed in this manner was cloned using PCR cloning vectors (PCR cloning kit—blunt end/ Roche Diagnostics) and examined by means of restriction analysis and sequencing.

Generation of the Triple Mutant Ser92Ala/His320Asn/ Gly322Phe

The triple mutant Ser92Ala/His320Asn/Gly322Phe was generated by combining the single mutant Ser92Ala and the double mutant His320Asn/Gly322Phe. For this the two mutated gene sequences which were each cloned into PCR cloning vectors (PCR cloning kit—blunt end/Roche Diagnostics) were cleaved separately from one another with the restriction endonucleases MunI and Asp718, and the restriction mixture was separated by means of agarose gel electrophoresis. MunI cleaves between the positions of the triplets of Ser92 and His320. A ca. 3700 bp long vector fragment was isolated from the single mutant Ser92Ala and a ca. 900 bp long fragment of the 3' region of the mutated gene sequence of the double mutant His320Asn/Gly322Phe was isolated from the agarose gel and these two fragments were ligated together in the next step. The resulting gene sequence was checked by sequencing.

EXAMPLE 2

Cloning of the Mutated Gene Sequences into the Expression Vector pPICZαA for *Pichia pastoris*

The verified mutated gene sequences were cleaved from the PCR cloning vectors by restriction with the restriction endonucleases EcoRI and Asp718, the restriction mixture was separated by means of agarose gel electrophoresis and the ca. 1480 bp long fragments were isolated from the agarose gel (QIAquick gel extraction kit/Qiagen). Subsequently the mutated gene sequences were ligated with the vector fragment from the expression vector pPICZαA which was also linearized with EcoRI and Asp718. The restriction endonuclease cleavage sites required for EcoRI and Asp718 were incorporated into the mutated gene sequences by the primers 5'-hAP and 3'-hAP which have recognition sequences for the restriction endonuclease EcoRI and Asp718 upstream and downstream respectively of the coding sequence. The resulting expression vectors for alkaline phosphatase mutants were designated as follows: pNaAP31-1 (Ser92Ala), pNaAP43-1 (Gly322Phe), pNaAP51-1 (His320Asn/Gly322Phe) and pNaAP6-1 (Ser92Ala/His320Asn/Gly322Phe).

In this vector the mutated gene sequences are under the control of the AOX 1 promoter (promoter for alcohol oxidase 1 from *Pichia pastoris*) which can be induced with methanol and is cloned in the correct reading frame behind the signal peptide of the α factor from *Saccharomyces cerevisiae*. The gene fragment inserted in this manner was then examined by means of restriction analysis and sequencing for an error-free base sequence. The resulting expression vectors which each encode one of the mutated gene sequences according to SEQ ID NO's.: 8-11, code for eukaryotic alkaline phosphatase mutants are shown with pNaAP31-1 as an example (see FIG. 1).

Transformation of the Expression Vectors Containing the Mutated Gene Sequences in *Pichia pastoris*

In order to transform the expression vectors containing mutated gene sequences in *Pichia pastoris* X-33 with subsequent integration into the genome, the vectors were firstly linearized with SacI (Roche Diagnostics GmbH). The transformation was carried out by means of electroporation using a Gene Pulser II (Biorad).

For this a colony of *Pichia pastoris* wild type strain was inoculated in 5 ml YPD medium (Invitrogen) and incubated at 30° C. overnight while shaking. The overnight culture was subsequently inoculated 1:2000 in 200 ml fresh YPD medium (Invitrogen) and incubated overnight at 30° C. while shaking until an $OD_{600}$ of 1.3-1.5 was reached. The cells were centrifuged (1500×g/5 minutes) and the pellet was suspended in 200 ml ice-cold sterile water (0° C.). The cells were again centrifuged (1500×g/5 minutes) and resuspended in 100 ml ice-cold, sterile water. The cells were again centrifuged and resuspended in 10 ml ice-cold (0° C.) 1 M sorbitol (ICN). The cells were again centrifuged and resuspended in 0.5 ml ice-cold (0° C.) 1 M sorbitol (ICN). The cells obtained in this manner were kept on ice and used immediately for the transformation.

About 1 μg linearized expression vector DNA was added to 80 μl of the cells and the entire mixture was transferred into an ice-cold (0° C.) electroporation cuvette and incubated for a further 5 minutes on ice. The cuvette was subsequently transferred to a Gene Pulser II (Biorad) and the transformation was carried out at 1 kV, 1 kΩ and 25 μF. After the electroporation, 1 ml 1 M sorbitol (ICN) was added to the mixture and subsequently 100 to 150 μl was plated out on a YPDS agar plate (Invitrogen) containing 100 μg/ml Zeocin (Invitrogen). The plates were subsequently incubated for 2-4 days at 30° C.

The clones were inoculated onto raster MD (=minimal dextrose) plates and analysed further. Grown clones were picked, resuspended in 20 μl sterile water, lysed (1 hour, 37° C.) with 17.5 U lyticase (Roche Diagnostics GmbH) and directly examined by means of PCR for the correct integration of the expression cassette containing an appropriately mutated gene sequence.

Clones which had integrated the complete expression cassette into the genome in the transformation were then used in expression experiments.

EXAMPLE 3

Expression of the Alkaline Phosphatase Mutants

Positive clones were inoculated in 3 ml BMGY medium (Invitrogen) and incubated overnight at 30° C. while shaking. Subsequently the OD at 600 nm was determined and the inoculation in 10 ml BMMY medium (Invitrogen) was carried out in such a manner that it resulted in an $OD_{600}$ of 1. The BMMY medium (Invitrogen) contains methanol (Mallinckrodt Baker B.V.) which induces the expression of the alkaline phosphatase mutants via the AOX 1 promoter.

The shaking flasks were incubated at 30° C. while shaking, samples were removed every 24 hours, the $OD_{600}$ was determined, an activity test was carried out for the expression of the alkaline phosphatase mutants and each time 0.5% methanol (Mallinckrodt Baker B.V.) was refed for further induction. The expression experiments were carried out for 96 hours.

EXAMPLE 4

Test for the Activity of Alkaline Phosphatase Mutants

500 µl aliquots of the expression culture of example 3 were removed, the $OD_{600}$ was determined and the cells were centrifuged. The supernatant was stored and the cell pellet was resuspended in a quantity of Y-PER™ (50 to 300 µl/Pierce) according to the $OD_{600}$ for lysis and shaken for 1 hour at room temperature. Subsequently the lysate was centrifuged in order to separate the cell debris (15000×g/5 minutes) and the supernatant was transferred to fresh reaction vessels. 5 µl of the lysate was then used in the activity test.

The activity test functions according to the following principle:

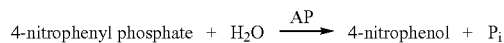

The absorption increase at 405 nm is measured.

50 µl 4-nitrophenyl phosphate solution (0.67 mol/l 4-nitrophenyl phosphate, Na salt (Roche Diagnostics GmbH) is added to 3 ml diethanolamine buffer (1 mol/l diethanolamine (Merck) pH 9.8, 0.5 mmol/l $MgCl_2$ (Riedel de Haen)) and the mixture was incubated at 37° C. Subsequently the reaction was started by adding 5 µl lysate and the change in absorbance at 37° C. was determined for 3 minutes and the ∆A/min was calculated from this.

The activity was then calculated according to the following formula:

$$\text{activity} = \frac{3.10}{\epsilon \times 0.005 \times 1} \times \Delta A/\min \times \frac{1}{\text{factor } x} \text{ [U/ml sample solution]}$$

$\epsilon = 18.2 \text{ } [1 \times \text{mmol}^{-1} \times \text{cm}^{-1}]$ factor $x$ = concentration factor after cell lysis The activity of the medium supernatant of the expression cultures was determined in a similar manner. In this case the reaction was also started with 50 µl supernatant but 0.5 mM $ZnCl_2$ was additionally added. The activity was then calculated without using factor x. Supernatants of clones which express highly-active alkaline phosphatase according to SEQ ID NO: 3 were used as a positive control and clones which were transformed with the initial vector pPICZαA without a target gene were used as a negative control.

The residual activity of the mutants was determined with this activity test as follows:
single mutant Ser92Ala: reduction of the specific activity by ca. 5000-fold
single mutant Gly322Phe: reduction of the specific activity by ca. 2500-fold
double mutant His320Asn/Gly322Phe: reduction of the specific activity by ca. 10000-fold (near to the detection limit)
triple mutant Ser92Ala/His320Asn/Gly322Phe: reduction of the specific activity by ca. 10000-fold (near to the detection limit).

EXAMPLE 5

Detection of the Expression of the AP Mutants by Western-Blot

10 µl unconcentrated supernatant or crude extract after cell lysis was applied to a 10% SDS gel (Novex Pre-Cast gel/Invitrogen) and the proteins that were present were separated according to size by applying an electrical field. The proteins separated in this manner were blotted onto a nitrocellulose membrane (Novex Western Transfer Apparatus XCell II Blot Module/Invitrogen). After the blotting the membrane was washed twice with 20 ml high-purity water for 5 minutes and subsequently shaken for 30 minutes in 10 ml blocking solution (Invitrogen). The membrane was then again washed twice for 5 minutes with 20 ml high-purity water, and subsequently incubated for 1 hour in 10 ml blocking solution (Invitrogen) which this time contained antibody 1 (anti-AP-rabbit/Rockland Inc. diluted from a 10 mg/ml stock solution 1:5000). It was then washed four times for 5 minutes each time with 20 ml of an antibody wash solution (Invitrogen) and subsequently the membrane was incubated for 30 min with 10 ml of a secondary antibody solution (contains the anti-rabbit antibody/Invitrogen). This was followed by a four-fold wash for 5 minutes each time with 20 ml of an antibody wash solution (Invitrogen) and a three-fold wash with 20 ml high-purity water for 2 minutes each time. The membrane was then incubated for 1-60 minutes with a dye solution (chromogenic substrate/Invitrogen) for the staining. The incubation period depends on the quality of the stain. After optimal staining, the membrane is washed three times with 20 ml high-purity water for 2 minutes each time and subsequently the membrane is dried at room temperature. All solutions with the exception of the high-purity water were derived from the Western Breeze chromogenic immunodetection kit from Invitrogen, all incubation steps were carried out at room temperature. The procedure was according to the instructions of the manufacturer.

EXAMPLE 6

Increasing the Expression Rate by Multiple Transformation

The best clones from the expression experiments were in turn prepared for electroporation as described in example 2 and again transformed with 1 µg linearized expression vector vector DNA and the transformation mixture was plated out on YPDS agar plates (Invitrogen) containing 1000 to 2000 µg/ml Zeocin (Invitrogen). In this manner the selection pressure is increased to such an extent that only those clones can grow which have integrated several copies of the expression vector and thus also integrated several copies of the respective resistance gene (in this case Zeocin) into the genome. The Zeocin resistance protein is the product of the bleomycin gene of Streptoalloteichus hindusstanus (Chalmels, T. et al., Curr. Genet. 20 (1991), 309-314; Drocourt, D. et al., Nucleic Acid Research 18 (1990), 4009), which binds Zeocin in a stoichiometric concentration ratio and thus makes the cell resistant to Zeocin. The higher the concentration of Zeocin in the YPDS agar plates, the more resistance protein the cell has to generate in order to quantitatively bind the Zeocin and thus enable growth. This is possible when for example multiple copies of the resistance gene are integrated into the genome. Clones were inoculated on raster MD plates as described above and again examined as described in example 2 by means of PCR analysis for the correct integration of the respective expression cassette. Subsequently these clones were again tested as described in examples 4 and 5 for AP activity or by Western blot analysis.

EXAMPLE 7

Increasing the Expression Rate by Using a Second Selection Pressure

Increasing the Zeocin concentration above 2000 µg/ml does not lead to an improved expression rate of the alkaline phosphatase mutants. The gene copy number of the genes according to SEQ ID NO's: 8-11 which code for the alkaline phosphatase mutants and are codon-optimized for expression in yeast was further increased in the expression clones by integrating additional expression vectors into the genome of the expression clone from example 6 which had the highest expression rate which were selected by means of a second selection pressure, preferably G418 (Roche Diagnostics GmbH). For this purpose the entire expression cassette from pNaAP31-1 consisting of AOX 1 promoter signal peptide of the α factor from *Saccharomyces cerevisiae*, codon-optimized gene for the alkaline phosphatase mutants according to SEQ ID NO's: 8-11 and AOX 1 transcription termination region, was isolated by PCR using appropriately selected primers and, as described below, integrated into the vector pIC9K whose integration into the genome of *Pichia pastoris* was selected by means of G418 (Roche Diagnostics GmbH). The primers used in this case, 5' expr and 3' expr, have the sequences SEQ ID NO: 20 and SEQ ID NO: 21.

The PCR preparation was analysed by means of agarose gel electrophoresis, the gene fragment having the expected size was isolated (QIAquick gel extraction kit/Qiagen), recleaved with SacI and NotI (Roche Diagnostics GmbH), subsequently isolated again from the agarose gel (QIAquick gel extraction kit/Qiagen) and ligated into a vector fragment isolated from pPIC9K which had also been linearized with SacI/NotI (Roche Diagnostics GmbH). This ensures that the entire expression cassette from the respective expression vectors was present in an identical form in pPIC9K. The inserted fragment was examined by means of restriction analysis and sequencing with the flanking regions. The resulting expression vectors for alkaline phosphatase mutants were designated pNaAP31-2(Ser92Ala), pNaAP43-2 (Gly322Phe), pNaAP51-2 (His320Asn/Gly322Phe) and pNaAP6-2(Ser92Ala/His320Asn/Gly322Phe).

The clones with the highest AP mutant expression rate from the multiple transformation using Zeocin as the selection marker were prepared for electroporation as described in example 2 and transformed with 1 µg vector fragment pNaAP31-2 and derivatives linearized with SacI (Roche Diagnostics GmbH) as described in example 2. The transformation preparation was subsequently stored for 1 to 3 days at 4° C. in 1 M sorbitol (ICN) (to develop the G418 resistance) and then 100 to 200 µl was plated out on YPD plates (Invitrogen) containing 1, 2 or 4 mg/ml G418 (Roche Diagnostics GmbH) and incubated for 3 to 5 days at 30° C. The resulting clones were again examined as described above with the activity test for an increased expression of the eukaryotic alkaline phosphatase mutants.

What is claimed is:

1. A recombinant DNA coding for a mutant of eukaryotic alkaline phosphatase, wherein said DNA comprises the nucleic acid sequence of SEQ ID NO: 11.

2. A vector comprising a nucleic acid encoding an alkaline phosphatase, wherein said nucleic acid comprises SEQ ID NO: 11.

3. The vector of claim 2 wherein said vector is selected from the group of vectors consisting of pPICZαA, B, C; pPICZ, pPICZ-E, pPICZα-E; pPIC6, pPIC6αA, B, C; pGAPZ, pGAPZαA, B, C; pPIC9; pPIC9K, pPIC3.5, pPIC3.5K, pAO815, pMET, pMETαA, B, C; pYES-DEST52, pYES2.1/V5-His-TOPO, pYC2-E, pYES2.1-E; YES-vectors, pTEF1/Zeo, pTEF1/Bsd, and pNMT-TOPO.

4. A host cell transformed with the vector of claim 2 or 3.

5. The host cell of claim 4 wherein the cell is *Pichia pastoris*.

6. A method for producing a eukaryotic alkaline phosphatase in yeast cells comprising the steps:
   preparing a first vector construct and a second vector construct wherein the first and second vector constructs each comprise a recombinant DNA encoding the polypeptide of SEQ ID NO: 7, wherein the first vector construct comprises a resistance gene to a first selection marker and the second vector construct comprises a resistance gene to a second selection marker,
   transforming said yeast cells with the first and second vector constructs, wherein said transforming comprises:
      selecting transformants which have integrated DNA from the first vector construct into a genome of the yeast cells by selected growth of the yeast cells on nutrient medium containing a low concentration of a first selection marker, increasing copy number of the integrated DNA from the first vector construct by multiple transfections of the yeast cells and further selected growth of the yeast cells on nutrient medium containing increased concentrations of a first selection marker,
      selecting transformants which have integrated DNA from the second vector construct into the genome of the host cell by selected growth of the yeast cells on nutrient medium containing low concentration of a second selection marker, and
      increasing copy number of the integrated DNA from the second vector construct by multiple transfections of the yeast cells and further selected growth of the yeast cells on nutrient medium containing increased concentrations of a second selection marker,
   expressing the alkaline phosphatase, and
   purifying the alkaline phosphatase.

7. The method of claim 6 wherein methylotrophic yeast cells are used.

8. The method of claim 7 wherein *Pichia pastoris* is used as the yeast cell.

9. The method of claim 6 wherein the first and second vectors are independently selected from the group of vectors consisting of: pPICZαA, B, C; pPICZ, pPICZ-E, pPICZα-E; pPIC6, pPIC6αA, B, C; pGAPZ, pGAPZαA, B, C; pPIC9; pPIC9K, pPIC3.5, pPIC3.5K, pAO815.

10. An isolated polynucleotide encoding the polypeptide of SEQ ID NO: 7.

11. A vector comprising the polynucleotide of claim 10.

12. The vector of claim 11 wherein the vector is selected from the group consisting of pPICZαA, B, C; pPICZ, pPICZ-E, pPICZα-E; pPIC6, pPIC6αA, B, C; pGAPZαA, B, C; pPIC9; pPIC9K, pPIC3.5, pPIC3.5K. pAO815, pMET, pMETαA, B, C; pYES-DEST52, pYES2.1/V5-His-TOPO, pYC2-E, pYES2.1-E; YES vectors, pTEF1/Zeo, pTEF1/Bsd, and pNMT-TOPO.

13. A host cell transformed with the vector of claim 11 or 12.

14. The host cell of claim 13 wherein the cell is *Pichia pastoris*.

* * * * *

SEQUENCE LISTING

<160> NUMBER OF SEQ ID NOS: 21

<210> SEQ ID NO 1
<211> LENGTH: 1464
<212> TYPE: DNA
<213> ORGANISM: Bos sp.
<220> FEATURE:
<221> NAME/KEY: CDS
<222> LOCATION: (1)..(1461)

<400> SEQUENCE: 1

```
ctc atc cca gct gag gag gaa aac ccc gcc ttc tgg aac cgc cag gca      48
Leu Ile Pro Ala Glu Glu Glu Asn Pro Ala Phe Trp Asn Arg Gln Ala
  1               5                  10                  15 gcc cag gcc ctt gat gta gcc aag aag ttg cag ccg atc cag aca gct      96
Ala Gln Ala Leu Asp Val Ala Lys Lys Leu Gln Pro Ile Gln Thr Ala
             20                  25                  30 gcc aag aat gtc atc ctc ttc ttg ggg gat ggg atg ggg gtg cct acg     144
Ala Lys Asn Val Ile Leu Phe Leu Gly Asp Gly Met Gly Val Pro Thr
         35                  40                  45 gtg aca gcc act cgg atc cta aag ggg cag atg aat ggc aaa ctg gga     192
Val Thr Ala Thr Arg Ile Leu Lys Gly Gln Met Asn Gly Lys Leu Gly
     50                  55                  60 cct gag aca ccc ctg gcc atg gac cag ttc cca tac gtg gct ctg tcc     240
Pro Glu Thr Pro Leu Ala Met Asp Gln Phe Pro Tyr Val Ala Leu Ser
 65                  70                  75                  80 aag aca tac aac gtg gac aga cag gtg cca gac agc gca ggc act gcc     288
Lys Thr Tyr Asn Val Asp Arg Gln Val Pro Asp Ser Ala Gly Thr Ala
                 85                  90                  95
```

```
act gcc tac ctg tgt ggg gtc aag ggc aac tac aga acc atc ggt gta       336
Thr Ala Tyr Leu Cys Gly Val Lys Gly Asn Tyr Arg Thr Ile Gly Val
            100                 105                 110 agt gca gcc gcc cgc tac aat cag tgc aac acg aca cgt ggg aat gag       384
Ser Ala Ala Ala Arg Tyr Asn Gln Cys Asn Thr Thr Arg Gly Asn Glu
        115                 120                 125 gtc acg tct gtg atc aac cgg gcc aag aaa gca ggg aag gcc gtg gga       432
Val Thr Ser Val Ile Asn Arg Ala Lys Lys Ala Gly Lys Ala Val Gly
130                 135                 140 gtg gtg acc acc acc agg gtg cag cat gcc tcc cca gcc ggg gcc tac       480
Val Val Thr Thr Thr Arg Val Gln His Ala Ser Pro Ala Gly Ala Tyr
145                 150                 155                 160 gcg cac acg gtg aac cga aac tgg tac tca gac gcc gac ctg cct gct       528
Ala His Thr Val Asn Arg Asn Trp Tyr Ser Asp Ala Asp Leu Pro Ala
                165                 170                 175 gat gca cag aag aat ggc tgc cag gac atc gcc gca cag ctg gtc tac       576
Asp Ala Gln Lys Asn Gly Cys Gln Asp Ile Ala Ala Gln Leu Val Tyr
            180                 185                 190 aac atg gat att gac gtg atc ctg ggt gga ggc cga atg tac atg ttt       624
Asn Met Asp Ile Asp Val Ile Leu Gly Gly Gly Arg Met Tyr Met Phe
        195                 200                 205 cct gag ggg acc cca gac cct gaa tac cca gat gat gcc agt gtg aat       672
Pro Glu Gly Thr Pro Asp Pro Glu Tyr Pro Asp Asp Ala Ser Val Asn
210                 215                 220 gga gtc cgg aag gac aag cag aac ctg gtg cag gaa tgg cag gcc aag       720
Gly Val Arg Lys Asp Lys Gln Asn Leu Val Gln Glu Trp Gln Ala Lys
225                 230                 235                 240 cac cag gga gcc cag tat gtg tgg aac cgc act gcg ctc ctt cag gcg       768
His Gln Gly Ala Gln Tyr Val Trp Asn Arg Thr Ala Leu Leu Gln Ala
                245                 250                 255 gcc gat gac tcc agt gta aca cac ctc atg ggc ctc ttt gag ccg gca       816
Ala Asp Asp Ser Ser Val Thr His Leu Met Gly Leu Phe Glu Pro Ala
            260                 265                 270 gac atg aag tat aat gtt cag caa gac cac acc aag gac ccg acc ctg       864
Asp Met Lys Tyr Asn Val Gln Gln Asp His Thr Lys Asp Pro Thr Leu
        275                 280                 285 gcg gag atg acg gag gcg gcc ctg caa gtg ctg agc agg aac ccc cgg       912
Ala Glu Met Thr Glu Ala Ala Leu Gln Val Leu Ser Arg Asn Pro Arg
290                 295                 300 ggc ttc tac ctc ttc gtg gag gga ggc cgc att gac cac ggt cac cat       960
Gly Phe Tyr Leu Phe Val Glu Gly Gly Arg Ile Asp His Gly His His
305                 310                 315                 320 gac ggc aaa gct tat atg gca ctg act gag gcg atc atg ttt gac aat      1008
Asp Gly Lys Ala Tyr Met Ala Leu Thr Glu Ala Ile Met Phe Asp Asn
                325                 330                 335 gcc atc gcc aag gct aac gag ctc act agc gaa ctg gac acg ctg atc      1056
Ala Ile Ala Lys Ala Asn Glu Leu Thr Ser Glu Leu Asp Thr Leu Ile
            340                 345                 350 ctt gtc act gca gac cac tcc cat gtc ttc tct ttt ggt ggc tac aca      1104
Leu Val Thr Ala Asp His Ser His Val Phe Ser Phe Gly Gly Tyr Thr
        355                 360                 365 ctg cgt ggg acc tcc att ttc ggt ctg gcc ccc ggc aag gcc tta gac      1152
Leu Arg Gly Thr Ser Ile Phe Gly Leu Ala Pro Gly Lys Ala Leu Asp
370                 375                 380 agc aag tcc tac acc tcc atc ctc tat ggc aat ggc cca ggc tat gcg      1200
Ser Lys Ser Tyr Thr Ser Ile Leu Tyr Gly Asn Gly Pro Gly Tyr Ala
385                 390                 395                 400 ctt ggg ggg ggc tcg agg ccc gat gtt aat ggc agc aca agc gag gaa      1248
Leu Gly Gly Gly Ser Arg Pro Asp Val Asn Gly Ser Thr Ser Glu Glu
                405                 410                 415
```

```
ccc tca tac cgg cag cag gcg gcc gtg ccc ctg gct agc gag acc cac      1296
Pro Ser Tyr Arg Gln Gln Ala Ala Val Pro Leu Ala Ser Glu Thr His
        420                 425                 430 ggg ggc gaa gac gtg gcg gtg ttc gcg cga ggc ccg cag gcg cac ctg      1344
Gly Gly Glu Asp Val Ala Val Phe Ala Arg Gly Pro Gln Ala His Leu
            435                 440                 445 gtg cac ggc gtg cag gag gag acc ttc gtg gcg cac atc atg gcc ttt      1392
Val His Gly Val Gln Glu Glu Thr Phe Val Ala His Ile Met Ala Phe
450                 455                 460 gcg ggc tgc gtg gag ccc tac acc gac tgc aat ctg cca gcc ccc gcc      1440
Ala Gly Cys Val Glu Pro Tyr Thr Asp Cys Asn Leu Pro Ala Pro Ala
465                 470                 475                 480 acc gcc acc agc atc ccc gac tag                                      1464
Thr Ala Thr Ser Ile Pro Asp
                485
```

<210> SEQ ID NO 2
<211> LENGTH: 487
<212> TYPE: PRT
<213> ORGANISM: Bos sp.

<400> SEQUENCE: 2

```
Leu Ile Pro Ala Glu Glu Asn Pro Ala Phe Trp Asn Arg Gln Ala
 1               5                  10                  15

Ala Gln Ala Leu Asp Val Ala Lys Lys Leu Gln Pro Ile Gln Thr Ala
                20                  25                  30

Ala Lys Asn Val Ile Leu Phe Leu Gly Asp Gly Met Gly Val Pro Thr
            35                  40                  45

Val Thr Ala Thr Arg Ile Leu Lys Gly Gln Met Asn Gly Lys Leu Gly
        50                  55                  60

Pro Glu Thr Pro Leu Ala Met Asp Gln Phe Pro Tyr Val Ala Leu Ser
 65                 70                  75                  80

Lys Thr Tyr Asn Val Asp Arg Gln Val Pro Asp Ser Ala Gly Thr Ala
                85                  90                  95

Thr Ala Tyr Leu Cys Gly Val Lys Gly Asn Tyr Arg Thr Ile Gly Val
            100                 105                 110

Ser Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Ala Ser Val Asn
    210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
            260                 265                 270
```

```
Asp Met Lys Tyr Asn Val Gln Gln Asp His Thr Lys Asp Pro Thr Leu
            275                 280                 285

Ala Glu Met Thr Glu Ala Ala Leu Gln Val Leu Ser Arg Asn Pro Arg
        290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
        355                 360                 365

Leu Arg Gly Thr Ser Ile Phe Gly Leu Ala Pro Gly Lys Ala Leu Asp
    370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
                405                 410                 415

Pro Ser Tyr Arg Gln Gln Ala Ala Val Pro Leu Ala Ser Glu Thr His
            420                 425                 430

Gly Gly Glu Asp Val Ala Val Phe Ala Arg Gly Pro Gln Ala His Leu
        435                 440                 445

Val His Gly Val Gln Glu Glu Thr Phe Val Ala His Ile Met Ala Phe
    450                 455                 460

Ala Gly Cys Val Glu Pro Tyr Thr Asp Cys Asn Leu Pro Ala Pro Ala
465                 470                 475                 480

Thr Ala Thr Ser Ile Pro Asp
                485

<210> SEQ ID NO 3
<211> LENGTH: 1476
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 3
gaattcttga ttccagctga agaagaaaat ccagctttt ggaatagaca agctgctcaa      60
gctttggatg ttgctaagaa gttgcaacca attcaaactg ctgctaagaa tgttattttg    120
tttttgggtg atggtatggg tgttccaact gttactgcta ctagaatttt gaagggtcaa    180
atgaatggta agttgggtcc agaaactcca ttggctatgg atcaatttcc atacgttgct    240
ttgtctaaga cttacaatgt tgatagacaa gttccagatt ctgctggtac tgctactgct    300
tacttgtgtg tgttaaggg taattacaga actattggta tttctgctgc tgctagatac    360
aatcaatgta atactactag aggtaatgaa gttacttctg ttattaatag agctaagaag    420
gctggtaagc tgttggtgt tgttactact actagagttc aacatgcttc tccagctggt    480
gcttacgctc atactgttaa tagaaattgg tactctgatg ctgatttgcc agctgatgct    540
caaaagaatg gttgtcaaga tattgctgct caattggttt acaatattgga tattgatgtt    600 attttgggtg gtggtagaat gtacatgttt ccagaaggta ctccagatcc agaatacccca   660 gatgatgctt ctgttaatgg tgttagaaag gataagcaaa atttggttca gaatggcaa     720 gctaagcatc aaggtgctca atatgtttgg aatagaactg ctttgttgca agctgctgat    780
```

```
gattctagtg ttactcattt gatgggtttg tttgaaccag ctgatatgaa gtataatgtt      840
caacaagatc atactaagga tccaactttg gctgaaatga ctgaagctgc tttgcaagtt      900
ttgtctagaa atccaagagg ttttttacttg tttgttgaag gtggtagaat tgatcatggt     960
catcatgatg gtaaggctta tatggctttg actgaagcta ttatgtttga taatgctatt     1020
gctaaggcta atgaattgac ttctgaattg gatactttga ttttggttac tgctgatcat     1080
agtcatgttt tttcttttgg tggttacact ttgagaggta cttctatttt tggtttggct     1140
ccaggtaagg ctttggatag taagtcttac acttctattt tgtatggtaa tggtccaggt     1200
tatgctttgg gtggtggttc tagaccagat gttaatggta gtactagtga agaaccatct     1260
tacagacaac aagctgctgt tccattggct agtgaaactc atggtggtga agatgttgct     1320 gttttttgcta gaggtccaca agctcatttg gttcatggtg ttcaagaaga aacttttgtt    1380
gctcatatta tggcttttgc tggttgtgtt gaaccataca ctgattgtaa tttgccagct     1440
ccagctactg ctactagtat tccagattaa ggtacc                               1476
```

<210> SEQ ID NO 4
<211> LENGTH: 487
<212> TYPE: PRT
<213> ORGANISM: Artificial Sequence
<220> FEATURE:
<223> OTHER INFORMATION: Description of Artificial Sequence: Synthetic construct

<400> SEQUENCE: 4

```
Leu Ile Pro Ala Glu Glu Asn Pro Ala Phe Trp Asn Arg Gln Ala
  1               5                  10                  15

Ala Gln Ala Leu Asp Val Ala Lys Lys Leu Gln Pro Ile Gln Thr Ala
             20                  25                  30

Ala Lys Asn Val Ile Leu Phe Leu Gly Asp Gly Met Gly Val Pro Thr
         35                  40                  45

Val Thr Ala Thr Arg Ile Leu Lys Gly Gln Met Asn Gly Lys Leu Gly
     50                  55                  60

Pro Glu Thr Pro Leu Ala Met Asp Gln Phe Pro Tyr Val Ala Leu Ser
 65                  70                  75                  80

Lys Thr Tyr Asn Val Asp Arg Gln Val Pro Asp Ala Ala Gly Thr Ala
                 85                  90                  95

Thr Ala Tyr Leu Cys Gly Val Lys Gly Asn Tyr Arg Thr Ile Gly Val
            100                 105                 110

Ser Ala Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
    130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Asp Ala Ser Val Asn
    210                 215                 220

Gly Val Arg Lys Asp Lys Gln Asn Leu Val Gln Glu Trp Gln Ala Lys
```

```
                225                 230                 235                 240
His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
                260                 265                 270

Asp Met Lys Tyr Asn Val Gln Gln Asp His Thr Lys Asp Pro Thr Leu
                275                 280                 285

Ala Glu Met Thr Glu Ala Ala Leu Gln Val Leu Ser Arg Asn Pro Arg
                290                 295                 300

Gly Phe Tyr Leu Phe Val Glu Gly Gly Arg Ile Asp His Gly His His
305                 310                 315                 320

Asp Gly Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
                340                 345                 350

Leu Val Thr Ala Asp His Ser His Val Phe Ser Phe Gly Gly Tyr Thr
                355                 360                 365

Leu Arg Gly Thr Ser Ile Phe Gly Leu Ala Pro Gly Lys Ala Leu Asp
                370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
                405                 410                 415

Pro Ser Tyr Arg Gln Gln Ala Ala Val Pro Leu Ala Ser Glu Thr His
                420                 425                 430

Gly Gly Glu Asp Val Ala Val Phe Ala Arg Gly Pro Gln Ala His Leu
                435                 440                 445

Val His Gly Val Gln Glu Glu Thr Phe Val Ala His Ile Met Ala Phe
                450                 455                 460

Ala Gly Cys Val Glu Pro Tyr Thr Asp Cys Asn Leu Pro Ala Pro Ala
465                 470                 475                 480

Thr Ala Thr Ser Ile Pro Asp
                485

<210> SEQ ID NO 5
<211> LENGTH: 487
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 5

Leu Ile Pro Ala Glu Glu Asn Pro Ala Phe Trp Asn Arg Gln Ala
  1               5                  10                  15

Ala Gln Ala Leu Asp Val Ala Lys Lys Leu Gln Pro Ile Gln Thr Ala
                 20                  25                  30

Ala Lys Asn Val Ile Leu Phe Leu Gly Asp Gly Met Gly Val Pro Thr
                 35                  40                  45

Val Thr Ala Thr Arg Ile Leu Lys Gly Gln Met Asn Gly Lys Leu Gly
     50                  55                  60

Pro Glu Thr Pro Leu Ala Met Asp Gln Phe Pro Tyr Val Ala Leu Ser
 65                  70                  75                  80

Lys Thr Tyr Asn Val Asp Arg Gln Val Pro Asp Ser Ala Gly Thr Ala
                 85                  90                  95
```

```
Thr Ala Tyr Leu Cys Gly Val Lys Gly Asn Tyr Arg Thr Ile Gly Val
            100                 105                 110

Ser Ala Ala Ala Arg Tyr Asn Gln Cys Asn Thr Thr Arg Gly Asn Glu
            115                 120                 125

Val Thr Ser Val Ile Asn Arg Ala Lys Lys Ala Gly Lys Ala Val Gly
            130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
                180                 185                 190

Asn Met Asp Ile Asp Val Ile Leu Gly Gly Gly Arg Met Tyr Met Phe
                195                 200                 205

Pro Glu Gly Thr Pro Asp Pro Glu Tyr Pro Asp Asp Ala Ser Val Asn
            210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
                260                 265                 270

Asp Met Lys Tyr Asn Val Gln Gln Asp His Thr Lys Asp Pro Thr Leu
                275                 280                 285

Ala Glu Met Thr Glu Ala Ala Leu Gln Val Leu Ser Arg Asn Pro Arg
            290                 295                 300

Gly Phe Tyr Leu Phe Val Glu Gly Gly Arg Ile Asp His Gly His His
305                 310                 315                 320

Asp Phe Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
                340                 345                 350

Leu Val Thr Ala Asp His Ser His Val Phe Ser Phe Gly Gly Tyr Thr
            355                 360                 365

Leu Arg Gly Thr Ser Ile Phe Gly Leu Ala Pro Gly Lys Ala Leu Asp
            370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
                405                 410                 415

Pro Ser Tyr Arg Gln Gln Ala Ala Val Pro Leu Ala Ser Glu Thr His
            420                 425                 430

Gly Gly Glu Asp Val Ala Val Phe Ala Arg Gly Pro Gln Ala His Leu
            435                 440                 445

Val His Gly Val Gln Glu Glu Thr Phe Val Ala His Ile Met Ala Phe
            450                 455                 460

Ala Gly Cys Val Glu Pro Tyr Thr Asp Cys Asn Leu Pro Ala Pro Ala
465                 470                 475                 480

Thr Ala Thr Ser Ile Pro Asp
                485

<210> SEQ ID NO 6
<211> LENGTH: 487
<212> TYPE: PRT
```

<213> ORGANISM: Artificial Sequence
<220> FEATURE:
<223> OTHER INFORMATION: Description of Artificial Sequence: Synthetic construct

<400> SEQUENCE: 6

```
Leu Ile Pro Ala Glu Glu Asn Pro Ala Phe Trp Asn Arg Gln Ala
 1               5                  10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Gly Lys Leu Gly
 50                  55                  60

Pro Glu Thr Pro Leu Ala Met Asp Gln Phe Pro Tyr Val Ala Leu Ser
 65                  70                  75                  80

Lys Thr Tyr Asn Val Asp Arg Gln Val Pro Asp Ser Ala Gly Thr Ala
            85                  90                  95

Thr Ala Tyr Leu Cys Gly Val Lys Gly Asn Tyr Arg Thr Ile Gly Val
           100                 105                 110

Ser Ala Ala Ala Arg Tyr Asn Gln Cys Asn Thr Thr Arg Gly Asn Glu
           115                 120                 125

Val Thr Ser Val Ile Asn Arg Ala Lys Lys Ala Gly Lys Ala Val Gly
       130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Asp Ala Ser Val Asn
210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
        275                 280                 285

Ala Glu Met Thr Glu Ala Ala Leu Gln Val Leu Ser Arg Asn Pro Arg
    290                 295                 300

Gly Phe Tyr Leu Phe Val Glu Gly Gly Arg Ile Asp His Gly His Asn
305                 310                 315                 320

Asp Phe Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
        355                 360                 365

Leu Arg Gly Thr Ser Ile Phe Gly Leu Ala Pro Gly Lys Ala Leu Asp
    370                 375                 380
```

```
Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
            405                 410                 415

Pro Ser Tyr Arg Gln Gln Ala Ala Val Pro Leu Ala Ser Glu Thr His
        420                 425                 430

Gly Gly Glu Asp Val Ala Val Phe Ala Arg Gly Pro Gln Ala His Leu
        435                 440                 445

Val His Gly Val Gln Glu Thr Phe Val Ala His Ile Met Ala Phe
    450                 455                 460

Ala Gly Cys Val Glu Pro Tyr Thr Asp Cys Asn Leu Pro Ala Pro Ala
465                 470                 475                 480

Thr Ala Thr Ser Ile Pro Asp
                485

<210> SEQ ID NO 7
<211> LENGTH: 487
<212> TYPE: PRT
<213> ORGANISM: Artificial Sequence
<220> FEATURE:
<223> OTHER INFORMATION: Description of Artificial Sequence: Synthetic
      construct

<400> SEQUENCE: 7

Leu Ile Pro Ala Glu Glu Asn Pro Ala Phe Trp Asn Arg Gln Ala
 1               5                  10                  15

Ala Gln Ala Leu Asp Val Ala Lys Lys Leu Gln Pro Ile Gln Thr Ala
            20                  25                  30

Ala Lys Asn Val Ile Leu Phe Leu Gly Asp Gly Met Gly Val Pro Thr
        35                  40                  45

Val Thr Ala Thr Arg Ile Leu Lys Gly Gln Met Asn Gly Lys Leu Gly
    50                  55                  60

Pro Glu Thr Pro Leu Ala Met Asp Gln Phe Pro Tyr Val Ala Leu Ser
65                  70                  75                  80

Lys Thr Tyr Asn Val Asp Arg Gln Val Pro Asp Ala Ala Gly Thr Ala
                85                  90                  95

Thr Ala Tyr Leu Cys Gly Val Lys Gly Asn Tyr Arg Thr Ile Gly Val
            100                 105                 110

Ser Ala Ala Ala Arg Tyr Asn Gln Cys Asn Thr Thr Arg Gly Asn Glu
        115                 120                 125

Val Thr Ser Val Ile Asn Arg Ala Lys Lys Ala Gly Lys Ala Val Gly
    130                 135                 140

Val Val Thr Thr Thr Arg Val Gln His Ala Ser Pro Ala Gly Ala Tyr
145                 150                 155                 160

Ala His Thr Val Asn Arg Asn Trp Tyr Ser Asp Ala Asp Leu Pro Ala
                165                 170                 175

Asp Ala Gln Lys Asn Gly Cys Gln Asp Ile Ala Ala Gln Leu Val Tyr
            180                 185                 190

Asn Met Asp Ile Asp Val Ile Leu Gly Gly Gly Arg Met Tyr Met Phe
        195                 200                 205

Pro Glu Gly Thr Pro Asp Pro Glu Tyr Pro Asp Asp Ala Ser Val Asn
    210                 215                 220

Gly Val Arg Lys Asp Lys Gln Asn Leu Val Gln Glu Trp Gln Ala Lys
225                 230                 235                 240

His Gln Gly Ala Gln Tyr Val Trp Asn Arg Thr Ala Leu Leu Gln Ala
                245                 250                 255
```

Ala Asp Asp Ser Ser Val Thr His Leu Met Gly Leu Phe Glu Pro Ala
            260                 265                 270

Asp Met Lys Tyr Asn Val Gln Gln Asp His Thr Lys Asp Pro Thr Leu
            275                 280                 285

Ala Glu Met Thr Glu Ala Ala Leu Gln Val Leu Ser Arg Asn Pro Arg
            290                 295                 300

Gly Phe Tyr Leu Phe Val Glu Gly Gly Arg Ile Asp His Gly His Asn
305                 310                 315                 320

Asp Phe Lys Ala Tyr Met Ala Leu Thr Glu Ala Ile Met Phe Asp Asn
                325                 330                 335

Ala Ile Ala Lys Ala Asn Glu Leu Thr Ser Glu Leu Asp Thr Leu Ile
            340                 345                 350

Leu Val Thr Ala Asp His Ser His Val Phe Ser Phe Gly Gly Tyr Thr
            355                 360                 365

Leu Arg Gly Thr Ser Ile Phe Gly Leu Ala Pro Gly Lys Ala Leu Asp
            370                 375                 380

Ser Lys Ser Tyr Thr Ser Ile Leu Tyr Gly Asn Gly Pro Gly Tyr Ala
385                 390                 395                 400

Leu Gly Gly Gly Ser Arg Pro Asp Val Asn Gly Ser Thr Ser Glu Glu
                405                 410                 415

Pro Ser Tyr Arg Gln Gln Ala Ala Val Pro Leu Ala Ser Glu Thr His
            420                 425                 430

Gly Gly Glu Asp Val Ala Val Phe Ala Arg Gly Pro Gln Ala His Leu
            435                 440                 445

Val His Gly Val Gln Glu Glu Thr Phe Val Ala His Ile Met Ala Phe
            450                 455                 460

Ala Gly Cys Val Glu Pro Tyr Thr Asp Cys Asn Leu Pro Ala Pro Ala
465                 470                 475                 480

Thr Ala Thr Ser Ile Pro Asp
                485

<210> SEQ ID NO 8
<211> LENGTH: 1476
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 8
gaattcttga ttccagctga agaagaaaat ccagcttttt ggaatagaca agctgctcaa      60
gctttggatg ttgctaagaa gttgcaacca attcaaactg ctgctaagaa tgttattttg     120
tttttgggtg atggtatggg tgttccaact gttactgcta ctagaatttt gaagggtcaa     180
atgaatggta agttgggtcc agaaactcca ttggctatgg atcaatttcc atacgttgct     240
ttgtctaaga cttacaatgt tgatagacaa gttccagatg ctgctggtac tgctactgct     300
tacttgtgtg gtgttaaggg taattacaga actattggtg tttctgctgc tgctagatac     360
aatcaatgta atactactag aggtaatgaa gttacttctg ttattaatag agctaagaag     420
gctggtaagg ctgttggtgt tgttactact actagagttc aacatgcttc tccagctggt     480
gcttacgctc atactgttaa tagaaattgg tactctgatg ctgatttgcc agctgatgct     540
caaaagaatg ttgtcaaga tattgctgct caattggttt acaatatgga tattgatgtt     600
attttgggtg gtggtagaat gtacatgttt ccagaaggta ctccagatcc agaatacccca    660

-continued

```
gatgatgctt ctgttaatgg tgttagaaag gataagcaaa atttggttca agaatggcaa      720
gctaagcatc aaggtgctca atatgtttgg aatagaactg ctttgttgca agctgctgat      780
gattctagtg ttactcattt gatgggtttg tttgaaccag ctgatatgaa gtataatgtt      840
caacaagatc atactaagga tccaactttg gctgaaatga ctgaagctgc tttgcaagtt      900
ttgtctagaa atccaagagg ttttttacttg tttgttgaag gtggtagaat tgatcatggt      960
catcatgatg gtaaggctta tatggctttg actgaagcta ttatgtttga taatgctatt     1020
gctaaggcta atgaattgac ttctgaattg gatactttga ttttggttac tgctgatcat     1080
agtcatgttt tttctttttgg tggttacact ttgagaggta cttctatttt tggtttggct     1140
ccaggtaagg ctttggatag taagtcttac acttctattt tgtatggtaa tggtccaggt     1200
tatgctttgg gtggtggttc tagaccagat gttaatggta gtactagtga agaaccatct     1260
tacagacaac aagctgctgt tccattggct agtgaaactc atggtggtga agatgttgct     1320 gttttttgcta gaggtccaca agctcatttg gttcatggtg ttcaagaaga aacttttgtt     1380
gctcatatta tggcttttgc tggttgtgtt gaaccataca ctgattgtaa tttgccagct     1440
ccagctactg ctactagtat tccagattaa ggtacc                                1476
```

<210> SEQ ID NO 9
<211> LENGTH: 1476
<212> TYPE: DNA
<213> ORGANISM: Artificial Sequence
<220> FEATURE:
<223> OTHER INFORMATION: Description of Artificial Sequence: Synthetic construct

<400> SEQUENCE: 9

```
gaattcttga ttccagctga agaagaaaat ccagcttttt ggaatagaca agctgctcaa       60
gctttggatg ttgctaagaa gttgcaacca attcaaactg ctgctaagaa tgttattttg      120
tttttgggtg atggtatggg tgttccaact gttactgcta ctagaatttt gaagggtcaa      180
atgaatggta agttgggtcc agaaactcca ttggctatgg atcaatttcc atacgttgct      240
ttgtctaaga cttacaatgt tgatagacaa gttccagatt ctgctggtac tgctactgct      300
tacttgtgtg gtgttaaggg taattacaga actattggtg tttctgctgc tgctagatac      360
aatcaatgta atactactag aggtaatgaa gttacttctg ttattaatag agctaagaag      420
gctggtaagg ctgttggtgt tgttactact actagagttc aacatgcttc tccagctggt      480
gcttacgctc atactgttaa tagaaaattgg tactctgatg ctgatttgcc agctgatgct      540
caaaagaatg gttgtcaaga tattgctgct caattggttt acaatatgga tattgatgtt      600
attttgggtg gtggtagaat gtacatgttt ccagaaggta ctccagatcc agaatacca       660 gatgatgctt ctgttaatgg tgttagaaag gataagcaaa atttggttca agaatggcaa      720
gctaagcatc aaggtgctca atatgtttgg aatagaactg ctttgttgca agctgctgat      780
gattctagtg ttactcattt gatgggtttg tttgaaccag ctgatatgaa gtataatgtt      840
caacaagatc atactaagga tccaactttg gctgaaatga ctgaagctgc tttgcaagtt      900
ttgtctagaa atccaagagg ttttttacttg tttgttgaag gtggtagaat tgatcatggt      960
catcatgatt ttaaggctta tatgctttg actgaagcta ttatgtttga taatgctatt     1020
gctaaggcta atgaattgac ttctgaattg gatactttga ttttggttac tgctgatcat     1080
agtcatgttt tttctttttgg tggttacact ttgagaggta cttctatttt tggtttggct     1140
ccaggtaagg ctttggatag taagtcttac acttctattt tgtatggtaa tggtccaggt     1200
```

```
tatgctttgg gtggtggttc tagaccagat gttaatggta gtactagtga agaaccatct    1260
tacagacaac aagctgctgt tccattggct agtgaaactc atggtggtga agatgttgct    1320 gttttgcta gaggtccaca agctcatttg gttcatggtg ttcaagaaga aacttttgtt    1380
gctcatatta tggcttttgc tggttgtgtt gaaccataca ctgattgtaa tttgccagct    1440
ccagctactg ctactagtat tccagattaa ggtacc                              1476

<210> SEQ ID NO 10
<211> LENGTH: 1476
<212> TYPE: DNA
<213> ORGANISM: Artificial Sequence
<220> FEATURE:
<223> OTHER INFORMATION: Description of Artificial Sequence: Synthetic
      construct

<400> SEQUENCE: 10
gaattcttga ttccagctga agaagaaaat ccagcttttt ggaatagaca agctgctcaa      60
gctttggatg ttgctaagaa gttgcaacca attcaaactg ctgctaagaa tgttattttg     120
tttttgggtg atggtatggg tgttccaact gttactgcta ctagaatttt gaagggtcaa     180
atgaatggta agttgggtcc agaaactcca ttggctatgg atcaatttcc atacgttgct     240
ttgtctaaga cttacaatgt tgatagacaa gttccagatt ctgctggtac tgctactgct     300
tacttgtgtg gtgttaaggg taattacaga actattggtg tttctgctgc tgctagatac     360
aatcaatgta atactactag aggtaatgaa gttacttctg ttattaatag agctaagaag     420
gctggtaagg ctgttggtgt tgttactact actagagttc aacatgcttc tccagctggt     480
gcttacgctc atactgttaa tagaaattgg tactctgatg ctgatttgcc agctgatgct     540
caaaagaatg gttgtcaaga tattgctgct caattggttt acaatatgga tattgatgtt     600
attttgggtg gtggtagaat gtacatgttt ccagaaggta ctccagatcc agaataccca     660
gatgatgctt ctgttaatgg tgttagaaag gataagcaaa atttggttca agaatggcaa     720
gctaagcatc aaggtgctca atatgtttgg aatagaactg cttgttgca agctgctgat     780 gattctagtt ttactcattt gatgggtttg tttgaaccag ctgatatgaa gtataatgtt     840
caacaagatc atactaagga tccaactttg gctgaaatga ctgaagctgc tttgcaagtt     900
ttgtctagaa atccaagagg ttttttacttg tttgttgaag gtggtagaat tgatcatggt     960
cataatgatt ttaaggctta tatggctttg actgaagcta ttatgtttga taatgctatt    1020
gctaaggcta atgaattgac ttctgaattg gatactttga ttttggttac tgctgatcat    1080
agtcatgttt ttctcttttgg tggttacact ttgagaggta cttctatttt tggtttggct    1140
ccaggtaagg ctttggatag taagtcttac acttctattt tgtatggtaa tggtccaggt    1200
tatgctttgg gtggtggttc tagaccagat gttaatggta gtactagtga agaaccatct    1260
tacagacaac aagctgctgt tccattggct agtgaaactc atggtggtga agatgttgct    1320 gttttgcta gaggtccaca agctcatttg gttcatggtg ttcaagaaga aacttttgtt    1380
gctcatatta tggcttttgc tggttgtgtt gaaccataca ctgattgtaa tttgccagct    1440
ccagctactg ctactagtat tccagattaa ggtacc                              1476

<210> SEQ ID NO 11
<211> LENGTH: 1476
<212> TYPE: DNA
<213> ORGANISM: Artificial Sequence
<220> FEATURE:
<223> OTHER INFORMATION: Description of Artificial Sequence: Synthetic
      construct
```

-continued

<400> SEQUENCE: 11

```
gaattcttga ttccagctga agaagaaaat ccagcttttt ggaatagaca agctgctcaa      60
gctttggatg ttgctaagaa gttgcaacca attcaaactg ctgctaagaa tgttattttg     120
tttttgggtg atggtatggg tgttccaact gttactgcta ctagaatttt gaagggtcaa     180
atgaatggta agttgggtcc agaaactcca ttggctatgg atcaatttcc atacgttgct     240
ttgtctaaga cttacaatgt tgatagacaa gttccagatg ctgctggtac tgctactgct     300
tacttgtgtg gtgttaaggg taattacaga actattggtg tttctgctgc tgctagatac     360
aatcaatgta atactactag aggtaatgaa gttacttctg ttattaatag agctaagaag     420
gctggtaagg ctgttggtgt tgttactact actagagttc aacatgcttc tccagctggt     480
gcttacgctc atactgttaa tagaaattgg tactctgatg ctgatttgcc agctgatgct     540
caaaagaatg gttgtcaaga tattgctgct caattggttt acaatatgga tattgatgtt     600
attttgggtg gtggtagaat gtacatgttt ccagaaggta ctccagatcc agaataccca    660
gatgatgctt ctgttaatgg tgttagaaag gataagcaaa atttggttca agaatggcaa     720
gctaagcatc aaggtgctca atatgtttgg aatagaactg ctttgttgca agctgctgat     780
gattctagtg ttactcattt gatgggtttg tttgaaccag ctgatatgaa gtataatgtt     840
caacaagatc atactaagga tccaactttg gctgaaatga ctgaagctgc tttgcaagtt     900
ttgtctagaa atccaagagg ttttttacttg tttgttgaag gtggtagaat tgatcatggt    960
cataatgatt ttaaggctta tatggctttg actgaagcta ttatgtttga taatgctatt    1020
gctaaggcta atgaattgac ttctgaattg gatactttga ttttggttac tgctgatcat    1080
agtcatgttt tttctttttgg tggttacact ttgagaggta cttctatttt tggtttggct    1140
ccaggtaagg ctttggatag taagtcttac acttctattt tgtatggtaa tggtccaggt    1200
tatgctttgg gtggtggttc tagaccagat gttaatggta gtactagtga agaaccatct    1260
tacagacaac aagctgctgt tccattggct agtgaaactc atggtggtga agatgttgct    1320
gttttttgcta gaggtccaca agctcatttg gttcatggtg ttcaagaaga aacttttgtt    1380
gctcatatta tggcttttgc tggttgtgtt gaaccataca ctgattgtaa tttgccagct    1440
ccagctactg ctactagtat tccagattaa ggtacc                               1476
```

<210> SEQ ID NO 12
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 12

```
gcgcgaattc ttgattccag ctgaagaaga aaatccagct ttttgg                     46
```

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 13

```
gcgcggtacc ttaatctgga atactagtag cagtagctgg agctggc                    47
```

```
<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagatgctg ctggtactgc tactgc                                          26

<210> SEQ ID NO 15
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gcagtagcag taccagcagc atctggaact tgtc                                 34

<210> SEQ ID NO 16
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gatcatggtc atcatgattt taaggcttat atggc                                35

<210> SEQ ID NO 17
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gccatataag ccttaaaatc atgatgacca tgatc                                35

<210> SEQ ID NO 18
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gatcatggtc ataatgattt taaggcttat atggc                                35

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccatataag ccttaaaatc attatgacca tgatc                                35
```

```
<210> SEQ ID NO 20
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gcgcgcctag gagatctaac atccaaagac g                                    31

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgcgcgctag cggatccgca caaacgaag                                       29
```